(12) United States Patent
Aslin (10) Patent No.: US 7,833,441 B2
(45) Date of Patent: Nov. 16, 2010

(54) METHOD OF PRODUCING A POLYMERIC MATERIAL

(75) Inventor: David Charles Aslin, Derbyshire (GB)

(73) Assignee: Prometheus Developments Limited, Derbyshire (GB)

( * ) Notice: Subject to any disclaimer, the term of this patent is extended or adjusted under 35 U.S.C. 154(b) by 360 days.

(21) Appl. No.: 10/556,194

(22) PCT Filed: May 10, 2004

(86) PCT No.: PCT/GB2004/002010

§ 371 (c)(1),
(2), (4) Date: Jan. 13, 2006

(87) PCT Pub. No.: WO2004/099292

PCT Pub. Date: Nov. 18, 2004

(65) Prior Publication Data

US 2007/0102686 A1    May 10, 2007

(30) Foreign Application Priority Data

May 9, 2003 (GB) ................. 0310650.7
May 15, 2003 (GB) ................. 0311147.3

(51) Int. Cl.
*C09K 21/00* (2006.01)
(52) U.S. Cl. ..................................... 252/606
(58) Field of Classification Search .......... 256/606; 558/114, 113, 70, 87, 89
See application file for complete search history.

(56) References Cited

U.S. PATENT DOCUMENTS

| 2,272,668 | A | * | 2/1942 | Honel ....................... 554/79 |
| 2,767,732 | A | * | 10/1956 | Hodgson et al. ............ 137/426 |
| 3,256,240 | A | * | 6/1966 | Smith ......................... 528/108 |
| 3,309,427 | A | | 3/1967 | Zech et al. |
| 3,439,067 | A | | 4/1969 | Austin et al. |
| 3,671,304 | A | | 6/1972 | Mischutin |
| 3,764,577 | A | * | 10/1973 | Burns et al. ................. 524/712 |
| 3,783,133 | A | * | 1/1974 | Speranza .................... 521/159 |
| 4,026,810 | A | * | 5/1977 | Bost ............................ 252/606 |
| 4,098,741 | A | * | 7/1978 | Login .......................... 524/47 |
| 4,258,448 | A | * | 3/1981 | Reitz et al. ..................... 8/582 |
| 4,458,035 | A | * | 7/1984 | Hardy et al. ................ 521/107 |
| 5,387,655 | A | | 2/1995 | Aslin |
| 6,500,917 | B1 | * | 12/2002 | Saindane et al. ............ 528/400 |
| 6,512,133 | B1 | * | 1/2003 | Gotzmann et al. .......... 558/114 |
| 7,115,677 | B2 | * | 10/2006 | Harashina et al. .......... 523/205 |
| 7,214,811 | B2 | * | 5/2007 | Gotzmann et al. .......... 558/114 |

FOREIGN PATENT DOCUMENTS

| DE | 2739916 | 3/1979 |
| DE | 19540861 | 5/1997 |
| DE | 10112155 | 9/2002 |
| GB | 954792 | 4/1964 |
| GB | 1001495 | 8/1965 |

* cited by examiner

*Primary Examiner*—Daniel M Sullivan
*Assistant Examiner*—Chukwuma O Nwaonicha
(74) *Attorney, Agent, or Firm*—Chernoff, Vilhauer, McClung & Stenzel (57) ABSTRACT

A method for producing a polymeric material comprises reacting a first reactant with a second reactant. The first reactant comprises anhydrous phosphorous pentoxide and the second reactant comprises an alcohol. A method for producing a polymeric salt material comprises reacting a first reactant comprising an amine with a second reactant comprising a phosphate ester.

75 Claims, 3 Drawing Sheets

Generalised Reaction Sequence for PRP Form 1

METHOD OF PRODUCING A POLYMERIC MATERIAL

This is a national stage application filed under 35 USC 371 based on International Application No. PCT/GB2004/002010 filed May 10, 2004, and claims priority under 35 USC 119 of United Kingdom Patent Application No. 0310650.7 filed May 9, 2003 and United Kingdom Patent Application No. 0311147.3 filed May 15, 2003.

FIELD OF THE INVENTION

This invention relates to methods for producing polymeric materials and materials produced using the methods. More particularly but not exclusively, the invention relates to methods for producing phosphorus rich polymers and methods of producing phosphate esters such as partial phosphate esters.

BACKGROUND OF THE INVENTION

Intumescence is a process where, under the influence of heat, a solid substance transforms into a relatively rigid, expanded foam. This foam which has a substantially lower thermal conductivity than the original substance, by virtue of this expansion, is used as a means of providing fire protection. Intumescent products, in their current form, are applied to the surface of materials and structures requiring protection from fire.

The intumescent char consists of amorphous carbon, or carbon and graphite, and condensed phosphoric acids. The char itself is not combustible. The underlying theory is that if a polymeric material can be altered so that it thermally decomposes in the same manner as an intumescent, then it will be non-flammable.

Where a substance is flammable such as wood, plastics, glass reinforced plastics these materials will increase the fire load of a compartment, or allow flame to spread along the surface of the material, thus allowing the fire to spread to areas remote from the point of initiation.

There are two ways of reducing the fire risk. Firstly, flame retardant additives may be added to the material. Most flame retardant additives are expensive and they often detract from the properties of the base material.

Alternatively, a non-flammable coating can be applied to the surface. This is only satisfactory providing the fire regime is limited. If the film has no insulation value, heat will pass through the film to the flammable substrate until it out-gases or distorts, disrupting the film and exposing the substrate to the fire regime. Because intumescent coatings expand under fire regimes to provide an insulating layer, they prevent the passage of heat to the substrate. Char formation, as in wood, is known to cause substrates to be self limiting when involved in fire.

In order to provide protection from fire, intumescent fire-retarding compositions included in paints or other coatings are often applied to the surface of materials and structures requiring such protection. Intumescent fire retarding compositions act by expanding under the influence of heat, to form an expanded foam/char layer of relatively incombustible material. This incombustible layer serves as insulation and prevents ready access of oxygen to the material upon which it is applied, thus reducing or delaying the overheating and/or combustion of the material. Additionally, intumescent materials may be included in sealants such as caulk and, upon expanding to form a foam/char layer act as heat-resistant smoke seals.

Intumescent fire retarding compositions may comprise:

(a) a source of a non-volatile acid, usually ammonium polyphosphate, (b) an organic substance, for example a carbonific polyol that can be decomposed by the liberated acid from the ammonium polyphosphate to reduce to a source of carbon, and (c) A source of inert volatile gases to assist the formation of the foam/char is a spumescent. The source of the volatile gases can be, for example, melamine. The intumescent foam/char of a phosphorus catalysing intumescent system typically consists of amorphous carbon, or carbon and graphite and condensed phosphoric acids.

The underlying theory behind the work is to combine the functionalities of the phosphate catalysed system into a polymeric molecule that has both resinous and intumescent properties.

As the inefficient labile groups are absent and all the functionalities are in contact at the molecular scale then no transport problem exists. For example, during the reaction of a conventional phosphate catalysed intumescent, the polyol present is dehydrated by the liberated polyphosphoric acid.

Clearly a phosphate ester has to be formed as an intermediate before the carbonific can be dehydrated to carbon. This phosphate ester decomposes immediately it is formed because the reaction temperature is above the decomposition point of the ester. However, were the phosphate ester present in the original substance, then the reaction would commence at the lower decomposition point of the ester not at the decomposition temperature of the ammonium polyphosphate.

The integration of the binder, spumescent, carbonific and catalyst functionalities of a conventional intumescent into one polymeric molecule by creating stable phosphate esters of carbonific polyols, was achieved in the Intrinsically Intumescent Polymers (IIP). The predication of the behaviour of the IIP from the original urea phytic acid salts may be considered as a proof of the theory of molecular integration of intumescent functionalities.

If the behaviour of both a conventional intumescent material and an IIP based material is considered with respect to the weight losses that occur as the material is subject to a heating regime, then, the IIP formulation is 40% more efficient at producing its foam char than a conventional formulation. As the IIP activates at below 150° C., then the fire protection provided by the insulation is available earlier in the fire regime than with APP formulations.

The IIP process was designed to provide a means of cheaply synthesising partial phosphate esters without resource to the route normally used for synthesising trimester plasticisers where the starting point is phosphorus oxychloride or phosphorus trichloride. These latter processes are inappropriate to the output of highly viscous polymeric materials. The IIP partial phosphate esters are produced by a unique process of direct esterification.

SUMMARY OF THE INVENTION

According to one aspect of the invention, there is provided a polymeric material represented by the general formula:

Where R1 is an alkylene, R2 and R3 are selected from H+, alkylene, alkyl, alkyl glycol ether and N is between 0.75 and 10.

In this specification reference is made to carbonifics and carbonific polyols. Carbonific polyols are polyols that will reduce to carbon, rather than to gaseous fragments under anaerobic pyrolysis by oxidising acids. It is believed that, if the majority of the backbone of the polymer is in the form of potentially carbonific groups, then the polymer will pyrolise to carbon not to flammable fragments.

Within the patent literature, carbonifics are generally described as polyols where greater than 40% of the molecule weight is hydroxyl groups. Within conventional technology carbonific polyols are limited to pentaerythritol, its dimer and trimer, glycerol and sucrose.

However, within the above method carbonific polyols may be ethane diol, 1-3 Propane diol, glycerol, pentaerythritol and trimethylol propane. Ethane diol and propane diol trapped as phosphate esters behave as carbonific polyols within the system whereas they would volatilise before decomposition in conventional systems.

However, this specification of a "carbonific", is derived from previous workers as presented in all prior art and is inadequate. The understanding is that a structure that will reduce to carbon in the presence of a dehydrating acid is best described as a sequence of —C—C-bonds in which no single carbon atom is more than two atoms removed from a carbon atom that either carries a hydroxyl, an ether of the dehydrating inorganic acid group or a nitrogen which in itself is bonded to one other carbon.

The compounds 1,2-propane diol, inositol, glucose or any other saccharide, while being carbonific polyols within the standard definition, will not esterify in the same manner. Any polyol in which the calculation of the 40% hydroxyl functionality includes secondary alcohols, will decompose in any direct esterification system. Therefore, the patent literature is incorrect in its definition in another way. When describing esters of carbonific polyols, the preferred definition of the active materials is as "polyols in which the weight of the primary hydroxyls occupy 40% of the molecular weight".

According to another aspect of this invention, there is provided a process for producing a polymeric material comprising reacting a first reactant comprising a phosphorus providing material, with a second reactant, said second reactant comprising, or being capable of providing, a carbonific polyol or a functional equivalent of a polyol.

According to another aspect of this invention, there is provided a process for producing a polymeric material comprising reacting a first reactant comprising anhydrous phosphorus pentoxide, and a second reactant selected from the group consisting of (a) a diol and (b) ether and an alcohol. The ether is preferably a cyclic ether.

The alcohol used in the process may comprise an alcohol having an hydroxyl group, or a polyol, such as a diol. The cyclic ether may comprise ethylene oxide and/or propylene oxide and/or tetrahydrofuran and/or tetrahydropyran. Preferably, the cyclic ether comprises tetrahydrofuran.

In a first embodiment of the process that is the second aspect of the invention, the first and second reactants may react with each other to produce the polymeric material. The polymeric material desirably comprises a phosphate ester, preferably a partial phosphate ester.

The reaction of the first embodiment may be as follows:—

The alcohol used in this reaction may be a polyol such as a diol.

The polymeric material formed in the reaction of the first embodiment may be represented by the general formula:

In one embodiment of the polymeric material formed by the first reaction, R1 is an alkylene, where C is 3 or 4 and N is 1 and R2 and R3 are H+.

In another embodiment of the polymeric material formed by the first reaction, R1 is n-butylene, R2 is H+, R3 is n-, or iso-, butyl, iso-propyl or any mixture of these, and N is 0.75 to 4.

In a further embodiment of the polymeric material formed by the first reaction R1 is n-butylene and/or 2,2-dimethylene propylene in a mole ratio of greater than 3:1 and where R2 and R3 are ethyl, H+ and/or ethyl glycol ether chains, having an acid value of 30 to 70 mg KOH/gm, and N is 2 to 10.

In a further embodiment of the polymeric material formed by the first reaction, R1 is n-butylene, R2 and R3 are ethyl and/or ethyl glycol ether chains and N is 2 to 10.

When the second reactant used to form the polymeric material formed by the first reaction comprises a cyclic ether and an alcohol, the alcohol may constitute an initiator to initiate a reaction between the first reactant and the cyclic ether. In addition, or alternatively, the alcohol may be a chain terminator in the polymeric material. The alcohol may be a carbonific material. Preferably, the carbonific material is converted to carbon when the resulting polymeric material including the carbonific material reaches its activation temperature, i.e. the temperature at which the product begins to intumesce. The alcohol, may be a short chain alcohol, and/or a polyol for example a diol.

In a second embodiment of the process that is the second aspect of the invention, the reaction may be as follows:

Preferably, the alcohol or diol of the second embodiment of the process has a chain length of four or less carbon atoms. This has the advantage of not forming flammable substances when the preferred embodiment of the polymeric material is exposed to fire conditions. Suitable alcohols for use as a second reactant may comprise one or more of methanol, ethanol, iso-propanol, N-propanol, N-butanol, iso-butanol. Suitable polyols for use as the second reactant may comprise one or more of pentaerythritol, glycerol, trimethalolpropane, ethane diol, 1,2-propane diol, 1,3-propane diol, 1,4-butane diol and glucose.

In the first of the process that is the second aspect, the diol may be provided in a reactor vessel. The first reactant may be added to the reactor vessel by a supply device. Preferably, the first reactant is held in a holding member, conveniently a hopper, and may be fed to the reactor by a feed device which may comprise a conduit. A pushing device may be mounted in the conduit for pushing the first reactant along the conduit. The pushing device may comprise a screw, such as an Archimedes screw.

Preferably, the feed device terminates in free space in the reactor vessel. An inert gas may be fed to the hopper and the feed device to prevent reaction of the first reactant with the second reactant in the feed device. The inert gas may be nitrogen.

In the second embodiment of the process that is the second aspect, the ether may be provided in the reactor vessel and the alcohol and the first reactant fed thereto. Preferably, the first reactant is added to the reactor vessel by a supply device. Preferably the first reactant is held in a holding member, desirably a hopper, and may be fed to the reactor vessel by a feed device, which may comprise a conduit. A pushing device may be mounted in the conduit for pushing the first reactant along the conduit. The pushing device may comprise a screw, such as an Archimedes screw. The alcohol may be fed to the reactor vessel by a drip feed device. If desired, a further alcohol may be provided in the reactor vessel.

Preferably, the first reactant and, where appropriate, the diol or alcohol are fed to the reactor vessel until the temperature of the reaction reaches a predetermined temperature. When such predetermined temperature is reached, the feeding of the first reactant and, where appropriate, the alcohol may be halted.

The reactor vessel may include a cooling device to cool the reactants. When the temperature of the reactants falls below the aforesaid predetermined temperature, the cooling device can be switched off and the feeding of the first and, where appropriate, the second reactants may be restarted.

Preferably, the reactants are heated to the aforesaid predetermined temperature.

The predetermined temperature may lie in the range of 25° C. to 65° C. In one embodiment, for example, where the first reactant and the diol produce the polymeric material, the temperature may lie within the range of 33° C. to 37° C., more preferably, substantially 35° C. In a further embodiment, for example, where the first reactant and the ether and alcohol produce the polymeric material, the predetermined temperature may lie in the range of 25° C. to 55° C., preferably in the range of 33° C. to 37° C., more preferably 35° C.

Desirably, the feeding of the first reactant and, where appropriate, the diol or alcohol may be halted or reduced when the temperature of the reaction mixture reaches substantially 37° C. The feeding of the reactants may be restarted when the temperature has dropped to substantially 33° C. The diol may comprise 1,3-propane diol.

Alternatively, the predetermined temperature may be in the range of 43° C. to 47° C., more preferably substantially 45° C. The feeding of the first reactant and where appropriate the alcohol may be halted or reduced when the temperature of the reaction mixture reaches substantially 47° C. The feeding of the reactants may be restricted when the temperature has dropped to substantially 43° C. In this embodiment, the second reactant may comprise 1,4-propane diol.

When all the ingredients have been added, the reaction mixture may be added to a temperature of between 55° C. to 75° C., more preferably to substantially 55° C., or substantially 75° C.

A stirring device may be provided in the reactor vessel to stir the reaction mixture.

A third reactant may be reacted with the product produced by the reaction of the first reactant and the second reactant. The third reactant may comprise a cyclic ether, for example, ethylene oxide, propylene oxide and/or glycidol. The reaction of the third reactant with the aforesaid reaction product may be as follows:

Where ΣXn=Y

Where the first reactant and the diol produce the polymeric material, the reactants are advantageously mixed with each other in stoichiometric ratios.

Where the first reactant and the ether and alcohol produce the polymeric material, the first reactant and the ether may be in a molar ratio of first reactant: ether in the range of 1:1 to 1•5:1, preferably between 1•1:1 to 1•2:1.

Where the reaction product of the first reactant, and the ether and alcohol are reacted with the third reactant, the first reactant and the ether may be in a molar ratio of first reactant: ether in the range of 1:1 to 2:1, preferably between 1•6:1 to 1•85:1. The reaction of the first reactant and the ether to produce the aforesaid reaction product may take place at a temperature in a range of 25° C. to 55° C., preferably in the range of 43° C. to 47° C., more preferably at substantially 45° C. The feeding of the first reactant and where appropriate, the alcohol may be halted or reduced when the temperature of the reaction mixture reaches substantially 47° C. The feeding of the reactants may be restarted when the temperature has dropped to substantially 43° C.

The reaction of the aforesaid reaction product with the third reactant may take place at a temperature in the range of 30° C. to 60° C., preferably 40° C. to 50° C.

Preferably, the reaction of the aforesaid reaction product with the third reactant is carried out in a second reactor vessel, which may comprise a vessel having an insulation jacket thereon, and may include a stirring device, for example, a rotor. Alternatively, the stirring device may provide a vortex within the polymeric material. The polymeric material may be provided within the second reactor vessel, and a feeder may be provided to feed the fourth reactant. The feeder may comprise a gas bubbler, which may be arranged within the second reactor vessel such that the third reactant is bubbled through the polymeric material. Alternatively, the feeder may comprise a gasification device, for example, a gasification tower, whereby an atmosphere of the third reactant is provided within the second reactor vessel. Preferably, the polymeric material flows through the atmosphere of the third reactant. A condensing device may be provided in the reactor vessel, whereby the condensing means allows the third reactant in the liquid phase to drop onto the polymeric material. The polymeric material may be held at a temperature above the boiling point of the third reactant. When the polymeric material is held at such a temperature, the third reactant volatilises on contacting the polymeric material and the gas is swept into the polymeric material by the stirring device.

According to another aspect of this invention, there is provided polymeric materials derived from the cross linking of oligomers of di ortho phosphate di-esters of 1,4-butane diol, containing four or more phosphorus atoms, derived from the reaction of phosphorus pentoxide with tetrahydrofuran and any primary or secondary alcohol or diol with four or less carbon atoms, or from the reaction of phosphorus pentoxide with 1,3-propane diol or 1,4-butane diol.

The phosphorus pentoxide is preferably anyhydrous pentoxide.

A proportion of the alcohols or diols may be replaced with pentaerythritol and/or trimethalol propane in order to achieve branched oligomers.

The oligomers may be subsequently modified by the reaction or the residual acid orthophosphate groups with cyclic ethers selected from ethylene oxide, propylene oxide and glycidol.

Uncondensed pyrophosphate groups may remain in or on the backbone of the oligomer.

According to another aspect of this invention, there is provided intumescent and flame retardant paints, varnishes and coatings derived from the phosphorus containing oligomers as described above, cross linked with urea or melamine formaldehyde resins.

The paints, varnishes and/or coatings may be water based i.e. having water as the main ingredient in which the other ingredients are dissolved or suspended or otherwise held.

According to another aspect of this invention, there is provided glues used in producing flame retardant particle boards, where the adhesive comprises the said oligomers as described above, cross linked with urea or melamine formaldehyde resins.

According to another aspect of this invention, there is provided phenolic casts, composites and foams derived from the curing of resol phenolic resins with the acid oligomers as described above.

According to another aspect of this invention, there is provided flame retardant and intumescent films and casts derived from the modified oligomers as described above where the residual acid orthophosphate groups are cross linked with cycloaliphatic epoxide resins.

According to another aspect of this invention, there is provided flame retardant and intumescent films and casts derived from the modified oligomers as described above in which the residual acid orthophosphate groups are cross linked with polyfunctional aziridines.

According to another aspect of this invention, there is provided flame retardant and intumescent films and casts derived from the modified oligomers as described above where the residual acid orthophosphate groups are cross linked with a zinc ammonia complex.

According to another aspect of this invention, there is provided flame retardant polyurethane films, casts and fibres derived from the oligomers as described above which are reduced in acid value to below 7 mg KOH/g with ethylene oxide and/or propylene oxide and then cross linked with isocyanates.

Preferably the flame retardant polyurethane films, casts and fibres may be derived from other polyols mixed with the oligomers prior to cross linking with isocyanates.

According to another aspect of this invention, there is provided flame retardant, rigid and flexible polyurethane foams derived from the oligomers as described above which are reduced in acid value to below 7 mg KOH/gm with ethylene oxide and/or propylene oxide, modified with water and cross linked with isocyanates.

Preferably the flame retardant, rigid and flexible polyurethane foams are formed from other polyols mixed with the oligomers prior to cross linking with isocyanates.

According to another aspect of this invention, there is provided flame retardant coatings, films and casts or fibres where the oligomers as described above reduced in acid value to below 7 mg KOH/g with ethylene oxide and/or propylene oxide, are mixed with other polymeric materials in order to render those coatings, films, casts or fibres flame retardant.

According to another aspect of this invention there is provided a process for the production of the oligomers as described above where the said reaction is undertaken by dispensing powdered phosphorus pentoxide into the stirred reaction mixture with the rate of addition being controlled in proportion to the temperature of the reaction mixture.

According to another aspect of this invention, there is provided a procedure for the reduction of the acid value of the oligomers as described above and/or other partial phosphate esters, where the ethylene and/or propylene oxide are contacted with the phosphate esters as a gas.

According to another aspect of this invention, there is provided a process for producing a polymeric salt material comprising a reacting an amine with a phosphate ester.

The process of producing the polymeric salt material may comprise reacting another reactant with the amine and the phosphate. Said other reactant may comprise an amine.

The, or each, amine may comprise an organic amine. Preferably, the, or each amine, comprises a polyamine and/or a polymer having an amine functional group. Preferably, the polymer has a plurality of amine functional groups.

The polyamine may comprise melamine.

The polymer having amine functional groups may comprise polyethyleneimine.

According to another aspect of this invention, there is provided a process for producing a polymeric material comprising reacting a melamine, a phosphate ester and polyethyleneimine.

The phosphate ester may comprise a partial phosphate ester. The phosphate ester may be a reaction product of phosphorus pentoxide, with 1,4-butane diol and/or 1,3-propane diol and/or 1,2-ethane diol, and/or pentaerythritol.

The phosphate ester may be a reaction product of condensed phosphoric acid with 1,4-butane diol and/or 1,3-propane diol and/or 1,2-ethane diol and/or pentaerythritol.

The polymeric material may comprise a polymeric salt, preferably a mixture of polymeric salts.

The preferred embodiment has the advantage that the polymeric material comprises a mixture of polymeric salt having a phosphorus content depending upon the ratio of melamine and polyethyleneimine amine used to react with the partial phosphate ester. The use of a low ratio of melamine to polyethylenemine results in the polymeric material having a higher content and a lower activation energy than the use of a high ratio of melamine to polyethylenemine.

In some embodiments, of the process for producing the polymeric salt material the reaction may be carried out at a temperature of up to 100° C., preferably between 85° C. and 98° C.

In other embodiments of the process for producing the polymeric salt material, the reaction may take place at a temperature of between 90° C. and 150° C., preferably at substantially 135° C.

The phosphate ester may comprise an orthophosphate.

The polymeric salt material may be capable of being suspended and/or dissolved in water to provide a pH of between 4 and 8.

The ratio of melamine to polyethyleneimine may be between 40% of the acids functionality neutralised with melamine and 60% of the acid functionality neutralised with polyethyleneimine. Preferably, the ratio of melamine to polyethyleneimine may be between 5% of the acid functionality neutralised with melamine and 95% of the acid functionality neutralised with polyethyleneimine.

According to another aspect of this invention, there is provided a flame retardant composition comprising a polymeric salt material as described above.

The polymeric salt material may be incorporated into a thermo setting or thermoplastic resin matrix.

BRIEF DESCRIPTION OF THE DRAWINGS

Embodiments of the invention will now be described by way of example only, with reference to the accompanying drawings, in which:—

DETAILED DESCRIPTION OF THE PREFERRED EMBODIMENTS

Figure 1:
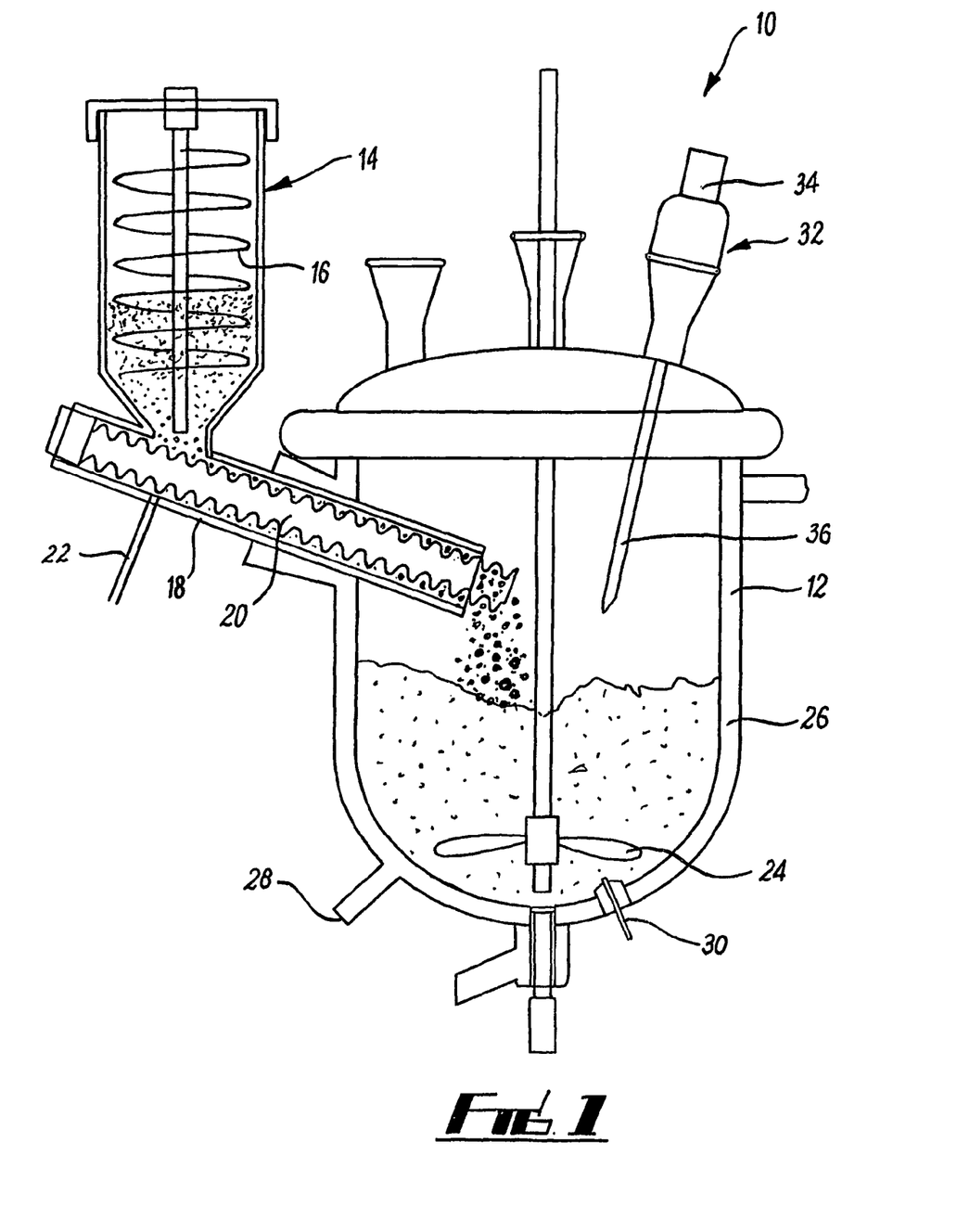
FIG. 1 is a diagrammatic view of apparatus for a first stage of a process for producing a polymeric material.

Referring to FIG. 1, there is shown a first apparatus 10 for a process for producing a polymeric material. The first apparatus 10 comprises a first reactor vessel 12 in which, in a first embodiment a diol such as 1,4-butane diol, can be dispensed, and in a second embodiment, a cyclic ether, such as tetrahydrofuran can be disposed as will be discussed below.

The first apparatus 10 further includes a hopper 14 in which the powdered anhydrous phosphorus pentoxide is held. The hopper 14 includes a mechanical agitator in the form of flexible PTFE wires 16. A feed tube 18 extends from the hopper 14 to free space within the first reactor vessel 12. The feed tube 18 includes an archimedes screw feeder 20 to drive the powdered anhydrous phosphorus pentoxide into the reactor vessel 12.

A nitrogen feed 22 is provided to supply nitrogen to the feed tube 18 thereby providing an inert atmosphere within the feed tube 18.

The reactor vessel 12 includes a stirrer 24 to stir the reactants in the vessel 12.

The vessel 12 has a hollow wall 26, and a coolant feed tube 28 is provided to feed a coolant, i.e. cold water to the hollow wall 26 to maintain the temperature of the reaction in the reactor vessel 12. A thermometer 30 is provided to monitor the temperature of the reaction and provide suitable signal to a controller to control the rate of feed of the coolant.

In the case of a second embodiment, when the reactant initially disposed in the reactor vessel 12 is, e.g., tetrahydrofuran, a dispenser 32 is provided to dispense an initiating and/or chain terminating alcohol (e.g. a diol) to the inside of the reactor vessel. The dispenser 32 comprises a funnel 34 and an elongate hollow tube 36 extends from the funnel 34 to the inside of the reactor vessel 12.

Figure 2:
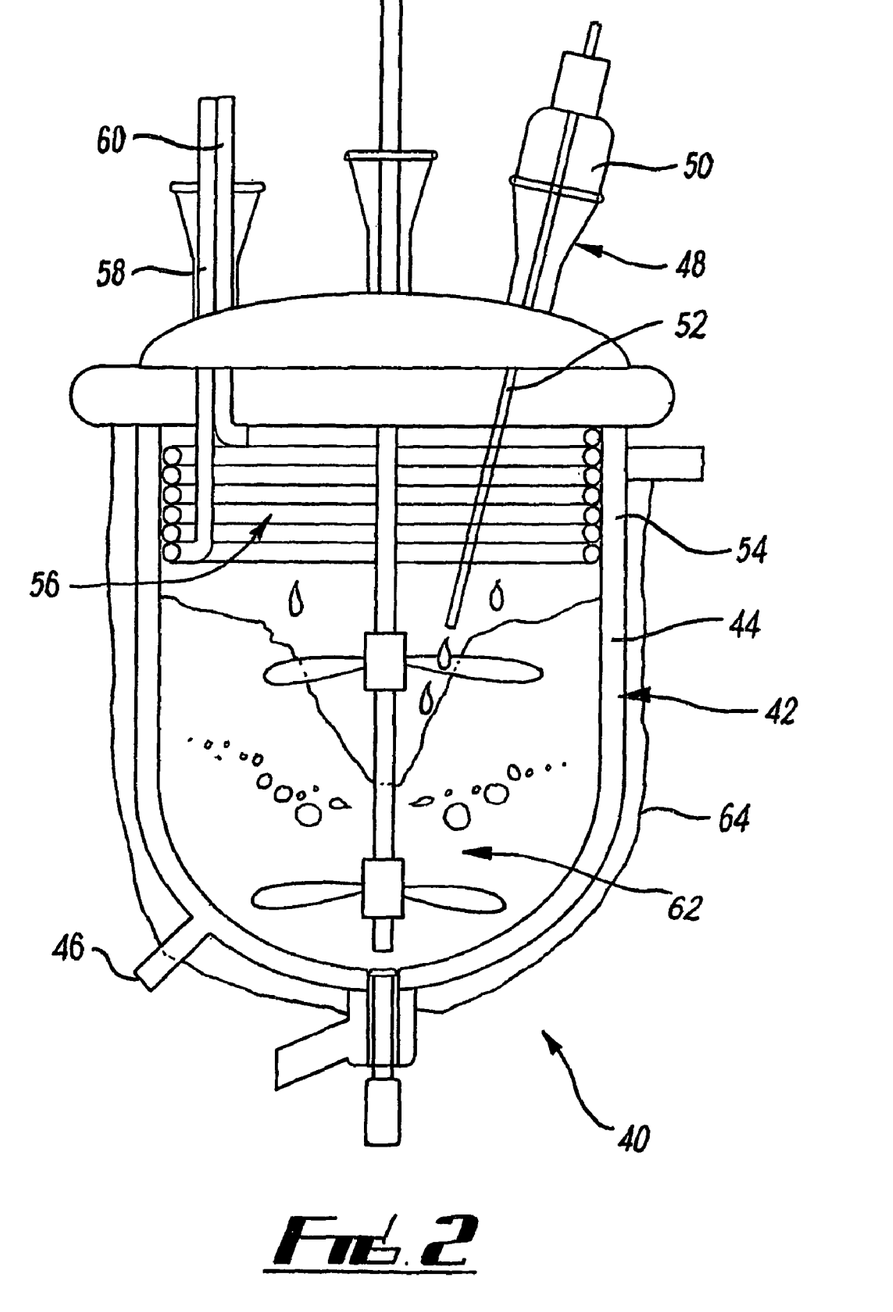
FIG. 2 is a diagrammatic view of apparatus for a second stage of a process for producing a polymeric material.

FIG. 2 shows a second apparatus 40 in which a reaction product for a reaction that occurs in the first apparatus 10 can be reacted with a third reactant in the form of a cyclic ether, such as ethylene oxide.

The second apparatus 40 comprises a second reactor vessel 42. The reaction product from the first reaction (which occurred in the first apparatus 10) can be disposed in the second reactor vessel 42. The second reactor vessel 42 has a hollow wall 44 to which a cooling fluid, e.g. water, can be supplied via a supply tube 46. A second dispenser 48 is provided to dispose liquid ethylene oxide into the second reactor vessel 42. The second dispenser 48 comprised a funnel 50 and an elongate hollow tube 52 extending from the funnel 50 to the inside of the second reactor vessel 42.

An upper region 54 of the second reactor vessel 42 is internally wound by a condenser coil 56 into which a coolant can be supplied via a supply tube 58. The coolant is exhausted from the coil via an exhaust tube 60.

A stirrer 62 is provided in the second reactor vessel 42 to stir the reactants. The second reactor vessel may be insulated by an insulating jacket 64.

The reaction load may be varied within considerable limits in order to achieve various structures and, without being limited to any theory, these may be calculated from the following considerations.

Each mole of phosphorus pentoxide may be considered to have 6 bonds in the form P—O—P Each mole of alcohol reacted to completion reduces the number of bonds in P—O—P by 2, yielding 1 bond as $POH^+$, and 1 bond as POR.

Each mole of primary diol reacted to completion reduces the number of bonds in P—O—P by 4, yielding 2 bonds as $POH^+$, and 2 bonds as $POR^{(O-P)}$ (This designation is used to indicate that the both ends of R are reacted as phosphate esters).

Each mole of tetrahydrofuran reacted to completion will reduce the number of $POH^+$ bonds by one, yielding a $POR^{(O-P)}$ and reduce the number of bonds in P—O—P by 2, yielding 1 bond as $POH^+$, and 1 bond as $POR^{(O-P)}$.

Thus if the number of gram moles of $P_2O_5$ in the reaction charge is W

And the number of gram moles of alcohol (or diols) is X

And the number of gram moles of 1,4-butane diol is Y

And the number of gram moles of tetrahydrofuran is Z

And the average gram molecular weight of the alcohols is M

Then:—

The number of P—O ($PO^{O-P}$) bonds in residual pyrophosphate bonds (per original mole of $P_2O_5$) A, is given by:—

$$A = (6W - 2X - 4Y - Z)/W$$

The number of $POH^+$ groups per original mole of $P_2O_5$, B, is given by:—

$$B = (X + 2Y - Z)/W$$

The number of POR groups per original mole of $P_2O_5$, C, is given by:—

$$C = X/W$$

The number of $POR^{(O-P)}$ groups per original mole $P_2O_5$, D, is given by:—

$$D = (2Y + Z)/W$$

The chain length, CL, is determined from the average number of chain extending groups (i.e. $POR^{(O-P)}$) per P atom which is given by:—

$$(A + D)/2W$$

If this figure is 2 the chain length is infinite. As the $PO_4$ is always terminal then:—

$$CL = \frac{4W + A + D}{4W - A - D}$$

The acid value (AV) may be calculated thus:—

$$AV = 56000B/(142W + XM + 90Y + 72Z)$$

The phosphorus content P % may be calculated:—

$$6200W/(142W + XM + 90Y + 72Z)$$

Various structures of the polymeric material are possible and may be defined according to their usage and cross linking mechanism in the following examples:—

Example 1

Phosphorus Rich Polymers (PRP) Form 1

When phosphorus pentoxide is decomposed to orthophosphate using an alcohol then the result is an equimolar mixture of the di and monoester.

$$P_2O_5 + 3ROH \Longrightarrow H_2RPO_4 + HR_2PO_4$$

The process is used for production of water treatment chemicals. If therefore, 1,4-butane diol is substituted for the alcohol and the reaction is undertaken in the stage 1 phosphorus pentoxide dispenser/reactor, the resulting product whose structure may be represented:

$$\text{HO} - \overset{\overset{O}{\|}}{\underset{OH}{P}} - O - R - O - \overset{\overset{O}{\|}}{\underset{OH}{P}} - O - R - O - \overset{\overset{O}{\|}}{\underset{OH}{P}} - O - R - O - \overset{\overset{O}{\|}}{\underset{OH}{P}} - O - OH$$

is produced very easily and appears as a medium viscosity pale brown resin.

Similar resins and variants are intended to be cross-linked with amino resins to produce low cost intumescent coatings.

The primary reactor vessel (as described above) is charged with multiples of 3 gram moles of 1,4-butane diol. Charge the powder feed hopper with similar multiples of 2 gram moles phosphorus pentoxide. Heat the vessel contents to 45° C. Start the stirrer.

The phosphorus pentoxide addition sequence is commenced. The stirrer speed is maintained at the minimum necessary to ensure rapid incorporation of the phosphorus pentoxide powder as it falls to the surface of the reaction mixture. The temperature controller should switch off the addition when the reaction mixture reaches 47° C. maximum and commence the flow of coolant to the reaction vessel jacket. When the temperature has fallen to 43° C. minimum the phosphorus pentoxide addition should be automatically recommenced by the controller. As the reaction proceeds and the product becomes more viscous the reaction temperature may be raised to 60° C. When all the phosphorus pentoxide has been added, the temperature is raised to 75° C. for four hours to complete the dissociation reaction.

The partial phosphate ester thus produced has an Acid Value of 600 mg KOH/gm. The product is either part of a two pack or a one pack heat curing material. For the purposes of Form 1, the product may equally be made by substituting 1,3 propane diol for the 1,4 butane diol and with subsequent adjustments to the following formulations with respect to acid value.

| Formulations using example 1 (units in parts by weight) | | | | | |
|---|---|---|---|---|---|
| | 1 | 2 | 3 | 4 | 5 |
| Form 1 as above | 100 | 100 | 100 | 100 | 100 |
| Pre reacted phosphoric acid | | 5 | | 5 | |
| Part Total | | 105 | | 105 | |
| BIP BT 338 | 79 | 81 | 65 | 67 | |
| BIP BT 970 | | | | | |
| BIP BT 640 | | | | | 95 |
| Part Total | 179 | 81 | 165 | 67 | 195 |
| Cure Temp | 80° C. | ambient | 100° C. | ambient | 90° C. |
| Cure Time | 15 mins | 24 hrs | 10 min | 1 hour | 15 mins |

Pre-reacted phosphoric acid is made by dissolving 15% by weight of aluminium hydroxide into commercial 70% phosphoric acid.

BT 338 (made by British Industrial Plastics Ltd (BIP)) is a typical commercially available partially etherified melamine formaldehyde resin BT 970 (made by British Industrial Plastics Ltd (BIP)) is a typical commercially available urea formaldehyde resin BT 640 (made by British Industrial Plastics Ltd (BIP)) is a typical commercially available etherified urea formaldehyde resin Formulation 1 as in example 1 is a single pack product that will produce heat curing intumescent films that are clear and flexible and will provide fire protection to flammable substrate by being applied to that substrate. It may be pigmented and modified with water or methoxy propanol as thinners.

Formulation 2 is a two part, air drying coating that will produce intumescent films that are clear and flexible and will provide fire protection flammable substrates. It may be pigmented and modified with water or methoxy propanol as thinners.

Formulation 3 is a heat curing glue for particle boards. If used to bind the wood fibres or flakes in hot press applications substituting this mixture for the conventional binder at 11-15% resin content, it will produce fire resistant particle boards.

Formulation 4 is a two pack air drying coating that will produce clear intumescent fire protective films on paper and cardboard or any flexible substrate that requires a temporary protection.

Formulation 5 is a single pack coating that will produce flexible fire retardancy to textiles and paper products. The oligomeric partial phosphate ester will unusually cross link with this typical example of a butylated urea formaldehyde resin under the condition given.

Figure 3:
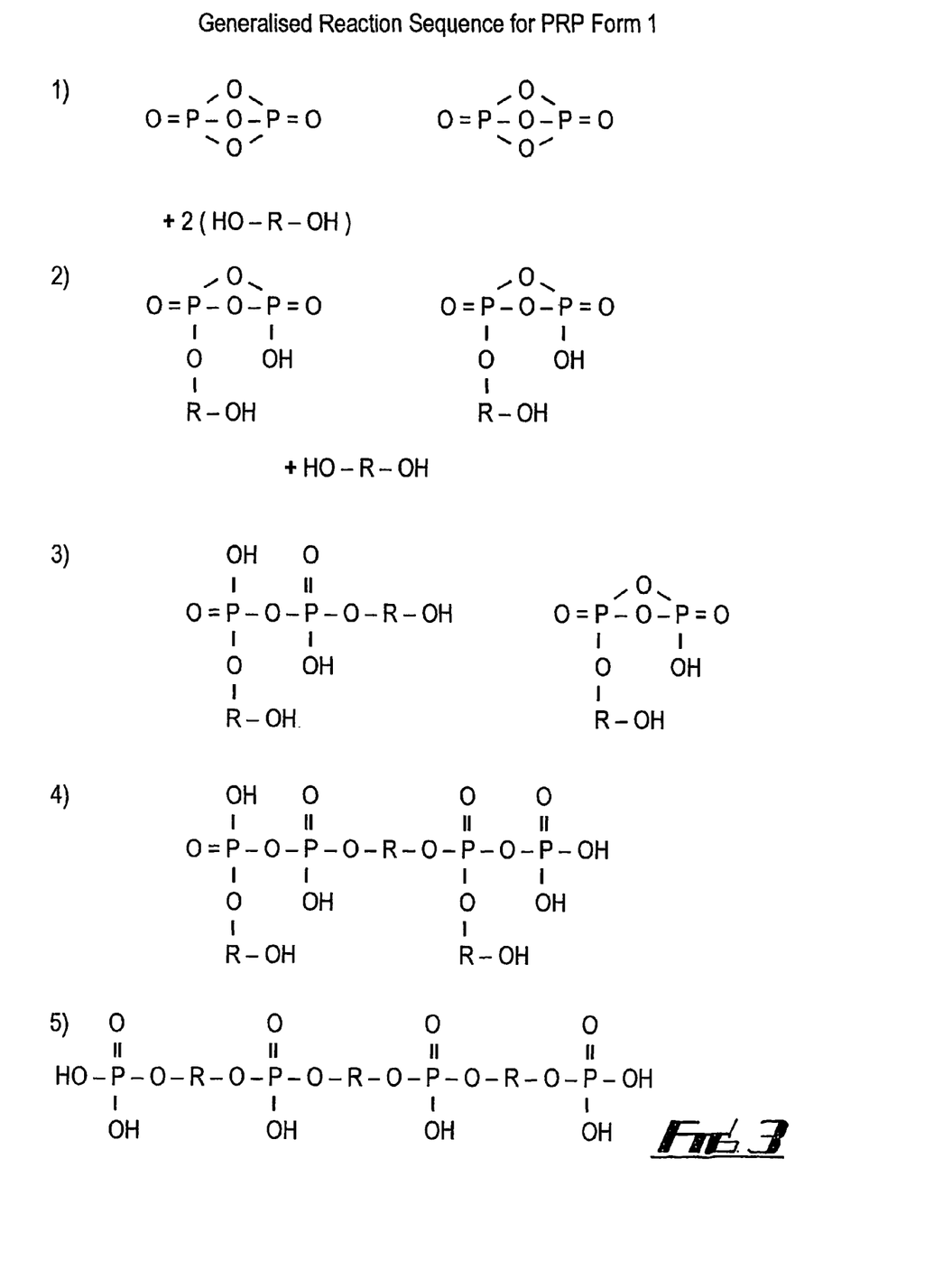
FIG. 3 shows a generalised reaction sequence for phosphorus rich polymers form 1

A generalised reaction sequence for PRP Form 1 is shown in FIG. 3.

Example 2

PRP Form 2

Form 2 products are curing agents and cross linkers for resol phenolic resins, significant variation in structure and chain length is possible to tailor these phenolic curing agents for different applications. Whereas Forms 3 and 4, below, preferentially utilise ethanol as the terminating and initiating alcohol the Form 2 oligomers utilises isopropanol or N butanol for this purpose, These alcohols lower the viscosity of the oligomer and, hence, the viscosity of the resin mixture. As resol phenolic resin are generally applied to fibre reinforced composites, the lower viscosity is useful in allowing penetration and wetting of the fibres. Additionally, it is useful to leave a small number of un-decondensed pyrophosphate bonds in the chain structure. This variant allows the resol phenolic resins to fully cure at room temperature by providing a constant level of acidity as the pyrophosphate decondenses under the influence of the water released when the resin condenses. The resins cured with these products are very pale and indicate advantages in tensile strength of the composites so produced.

Formulation A Using Example 2

The apparatus used is as described above. The phosphorus pentoxide hopper is charged with a multiple of 2 gram moles of phosphorus pentoxide. The reactor is charged with the same multiple of one gram mole of 1,4-butane diol and two gram moles of tetrahydrofuran. A separate funnel dispensing into the reactor is charged with the same multiple of 1 gram mole of isopropyl alcohol. Heat the vessel contents to 35° C. Start the stirrer.

Commence the phosphorus pentoxide addition sequence. The stirrer speed in maintained at the minimum necessary to ensure rapid incorporation of the phosphorus pentoxide powder as it falls to the surface of the reaction mixture. The proportional controller should switch off the addition when the reaction mixture reaches 37° C. maximum and commence the flow of coolant to the reaction vessel jacket. When the temperature has fallen to 33° C. minimum the phosphorus pentoxide addition should be automatically recommenced by the controller. As the reaction proceeds and the product becomes visually more viscous the isopropyl alcohol is drip fed into the reaction mixture to maintain viscosity control.

When all the phosphorus pentoxide and isopropyl alcohol has been added the temperature is raised to 55° C. for two hours to complete the dissociation reaction.

To use for cross linking cold curing phenolic resins the Form 2 product is added to aqueous resol resins such as Borden Chemicals Cellobond J2033L at between 5% and 25%, which will give cure times from 4 hours to 10 minutes at 20° C.

If non aqueous phenolic resols are used as taught in GB 2291881, then additions of between 10% and 30% will yield cure times of 5 hours to 25 minutes at 20° C. The effects on physical properties are as shown:—

| Cold Press laminates 2:1 resin to glass ratio 5 layers 60 g Chopped Strand Mat. | | | | |
|---|---|---|---|---|
| Resin | Curing System | Tensile Strength Pascals | Tensile Modulas Pascals | Elongation at Break % |
| Aqueous resol phenolic Resin | 10% Phencat 10 | 6.00E + 07 | 1.86E + 10 | 2.9 |
| Aqueous resol phenolic Resin | 15% Form 2 | 7.37E + 07 | 2.28E + 10 | 3.3 |
| Non aqueous resol phenolic resin | 20% Phencat 382 | 1.46E + 08 | 4.78E + 10 | 4.4 |
| Non aqueous resol phenolic resin | 10% Form 2 | 1.71E + 08 | 5.23E + 10 | 4.7 |
| Non aqueous resol phenolic resin | 15% Form 2 | 1.53E + 08 | 8.53E + 10 | 4.01 |
| Non aqueous resol phenolic resin | 20% Form 2 | 1.40E + 08 | 8.62E + 10 | 3.8 |

Phencat 10 is a conventional phosphoric acid/paratoluene sulfonic acid curing system. Phencat 382 is a partial phosphate ester as taught in EP 92309426.2

Formulation B Using Example 2

The apparatus used is as described above. The phosphorus pentoxide hopper is charged with a multiple of 1.5 gram moles of phosphorus pentoxide. The reactor is charged with the same multiple of two gram moles of tetrahydrofuran. A separate funnel dispensing into the reactor is charged with the same multiple of 2.5 gram mole of either iso butanol or N butanol. Heat the vessel contents to 35° C. Start the stirrer.

Commence the phosphorus pentoxide addition sequence. The stirrer speed in maintained at the minimum necessary to ensure rapid incorporation of the phosphorus pentoxide powder as it falls to the surface of the reaction mixture. The proportional controller should switch off the addition when the reaction mixture reaches 37° C. maximum and commence the flow of coolant to the reaction vessel jacket. When the temperature has fallen to 33° C. minimum the phosphorus pentoxide addition should be automatically recommenced by the controller. As the reaction proceeds and the product becomes more viscous the isopropyl alcohol is drip fed into the reaction mixture to maintain viscosity control.

When all the phosphorus pentoxide and isopropyl alcohol has been added the temperature is raised to 55° C. for two hours to complete the dissociation reaction.

The product contains no residual pyrophosphates but has a low viscosity, the product made with iso-butanol having a viscosity of less than 300 cP. The product with N butanol provides an exceptionally fast, low temperature cure when used with resol phenolic resins. However, the product made with iso-butanol gives very low strengths when used as a curing agent for phenolic resins but may be used to impregnate porous flammable substrates such as wood to provide excellent flame retardancy.

Phenolic foams are frequently used as fire resistant insulation panels. However, they tend to be very brittle and subject to very poor physical behaviour under fire conditions. The substitution of the Form 2 curing agents in conventional formulations using conventional art produces pale flexible phenolic foam, insulating board that can have sufficient flexibility to be used a structural core for sandwich laminates. Unlike conventionally produced phenolic foam these Form 2 cured phenolic foams have excellent behaviour under fire conditions with little tendency to deflagrate or contract.

Example 3

Forms 3 and 4

Form 3 materials are very low acid value partial phosphate esters designed to produce intumescent films, glues and coatings. Form 3 partial phosphate esters are cross-linked using additive reactions of the organic acid orthophosphate groups. The organic acid orthophosphates behave like carboxylic acids, and, hence, any system used for cross-linking carboxylic acid functional resins may be used with low acidity polymeric orthophosphate esters. Thus, cycloaliphatic epoxides, poly functional aziridines, poly carbodiimides, and zinc and zirconium ammonia complexes will cross link either at room or elevated temperature depending on the cross linking agent and the acid value.

Form 4 materials are pH neutral and hydroxyl functional. As such they react with isocyanates to give polyurethanes, thus giving non flammable, polyurethane products that are non-flammable within the usual test requirements. Depending on the selection and level of the isocyanate and the polyols with which it is blended Form 4, materials can produce foams suitable for soft furnishing foam production to produce non-flammable upholstery, or can be incorporated into PU fibres to produce flame retardant polyurethane fibres based on polytetrahydrofuran, such as sold under the trade mark LYCRA or ELASTANE, or into non flammable, light fast PU films.

Form 3 and 4 materials are made by reacting the residual acid orthophosphate functionalities with cyclic ethers. This second stage procedure does not alter the backbone structure of the oligomer. The properties of the oligomer, and any polymer or film produced from the oligomers, are dependent on the molecular structure of the precursor manufactured in the first reaction stage and the molar ratio of the components reacted at that stage. The neutral oligomers are primarily linear and, hence, give flexible foams and films. Further, the chain length of the linear oligomer determines the properties of the final polymer. An oligomer consisting of a chain of nine orthophosphate groups inter spaced with eight 1,4 butane diol esters creates flexible foams and elastomers when fully reacted with cyclic ethers and cross linked with isocyanates.

While these linear oligomers can be modified by the addition of high hydroxyl value polyols to form rigid foams, it is necessary to produce branched oligomers for the production of paint films. This is achieved by the incorporation of either pentaerythritol or trimethalol propane in the charge of initiating alcohols with the tetrahydrofuran at the start of the reaction. This leads to the production of ligand arms by chain extension from either pentaerythritol which gives four branches or trimethalol propane which gives a three branched oligomer.

Additionally, any of the additive cross linkers that may be used with carboxylic acid resins may be used with the Form 3 products. However, acid orthophosphates are highly reactive and an acid value of approximately or below 50 mgms KOH/gm is required. In order for this to be at least difunctional with acid orthophosphates the molecular weight of the form 3 oligomer should be about 2000.

Formulation A Using Example 3

The apparatus used is as above. The phosphorus pentoxide hopper is charged with a multiple of 6 gram moles of phosphorus pentoxide. The reactor is charged with the same multiple of 1 gram mole of pentaerythritol and the same multiple 8 gram moles of tetrahydrofuran. A separate funnel dispensing into the reactor is charged with the same multiple of 6 gram moles of ethanol. Heat the vessel contents to 45° C. Start the stirrer.

Commence the phosphorus pentoxide addition sequence. The stirrer speed in maintained at the minimum necessary to ensure rapid incorporation of the phosphorus pentoxide powder as it falls to the surface of the reaction mixture. The proportional controller should switch off the addition when the reaction mixture reaches 47° C. and commence the flow of coolant to the reaction vessel jacket. When the temperature has fallen to approximately 43° C. minimum the phosphorus pentoxide addition should be automatically recommenced by the controller. As the reaction proceeds and the product becomes more viscous the ethanol is drip fed into the reaction mixture to maintain viscosity control.

When all the phosphorus pentoxide and ethanol alcohol has been added the temperature is raised to 65° C. for two hours to complete the dissociation reaction. The reaction product will have an acid value of about 304 mg KOH/gm.

The reaction mixture is then transferred to the secondary reactor as described above. A total of the selected multiple of 12 moles of cyclic ether is required to reduce the acid value to approximately 50. This may be any molar combination of ethylene or propylene oxide. The preferred reaction temperature is between 55° C. and 65° C. It should be noted that as the acid value is reduced then so is the viscosity.

The table below shows some examples of conversions in the secondary reactor and the subsequent method of cure of the end product to yield clear, flame retardant films or intumescent varnishes and flexible coatings.

| Final Acid Value | 50 | 50 | 50 |
|---|---|---|---|
| Cross Linking Agent | XAMA 2 | ERL 4206 | Zn NH$_4$ Complex |
| Quantity | 7% | 10% | 15% |
| Cure condition | Ambient 10 minutes | 140° C. 15 minutes | variable |
| Film Properties | Clear hard intumescent | Glossy clear ductile | Hard translucent |
| Phosphorus content of film | 14.5% | 14.5% | 15% |

XAMA 2 is a commercial polyfunctional aziridine, the product of Flevo Chemie. ERL 4226 is a di functional cycloaliphatic epoxide and the product of Union Carbide. The zinc ammonia complex is composed of 7.2% zinc oxide, 8.7% ammonia solution and 12.7% ammonium carbonate in demineralised water.

Formulation B Using Example 3

The apparatus used is as described above. The phosphorus pentoxide hopper is charged with a multiple of 4.5 gram moles of phosphorus pentoxide. The reactor is charged with the same multiple of 8 gram moles of tetrahydrofuran and 0.5 gram moles of ethanol. A separate funnel dispensing into the reactor is charged with the same multiple of 5.0 gram mole of ethanol. Heat the vessel contents to 35° C. Start the stirrer.

The phosphorus pentoxide addition sequence is commenced. The stirrer speed in maintained at the minimum necessary to ensure rapid incorporation of the phosphorus pentoxide powder as it falls to the surface of the reaction mixture. The proportional controller should switch off the addition when the reaction mixture reaches 37° C. maximum and commence the flow of coolant to the reaction vessel jacket. When the temperature has fallen to 33° C. minimum the phosphorus pentoxide addition should be automatically recommenced by the controller. As the reaction proceeds the additional ethanol in the funnel is drip fed into the reaction mixture in approximate molar proportion to the phosphorus pentoxide.

When all the phosphorus pentoxide and ethanol has been added the temperature is raised to 65° C. for two hours to complete the dissociation reaction. The reaction product is transferred to the secondary reactor as in described above and treated with a further similar multiple of 8 moles ethylene oxide and or propylene oxide, by gaseous contact, as described above. The acid value of such neutral, phosphorus rich, hydroxyl functional oligomers must be below 7 mg KOH/g.

Such a material has a phosphorus content of 16.1%. It is not necessary to cross link all the polyols with isocyanate. When the product is cross linked with methyltoluene diisocyanate, with no other polyol present, it will give a phosphorus content of 12.9% The film is not only non-flammable, it is intumescent.

When the oligomer is modified with the addition of an appropriate foam control agent such as NIAX 264 (made by OSI) and approximately 1% water is added, the oligomer will form tough, resilient, flexible foam with either toluene diisocyanate (TDI) or MDI, suitable for upholstery use that is non flammable and emits very little smoke when exposed to a strong flame.

Formulations in which the embodiments as oligomers are present at only 30 pph of the polyols will still provide adequate flame retardant properties to about the level required of combustion modified foams under United Kingdom requirements but will either be flexible or rigid depending on the hydroxyl number of the polyol.

When the precursor described above is reacted with sufficient ethylene oxide to reduce the acid value to below 7 mg KOH/g rather than 50, then the branched oligomer may be used to form flame retardant paints and varnishes. The oligomer is soluble in most ketones and, hence, may be blended with other film forming polyols such as Bayer Desmophen 800 or used on its own. It may be cross linked with the stochiometrically correct level of either diphenyl methane diisocyanate (MDI), isophorone diisocyanate or trimethyl hexamethylene diisocyanate and may be catalysed with any of the systems that are conventional art. The PRP Form 4 polyols may be treated as would any other polyol used in conventional polyurethane technology within the limits of its compatibility.

Formulation C Using Example 3

Form 4 may be used as a flame retardant for low melting point thermoplastics without the need to cross link the hydroxyl functionalities. A oligomer was produced as described above. This was added at the rate of 15% by weight to polystyrene beads. The mass was gently heated until a rubbery mass was obtained. This was cooled and rendered into granules by grinding in a mortar and pestle. The mass was then hot pressed into flat sheets. While the sheets were distinctly brown when compared to unmodified polystyrene sheet they exhibited a substantial degree of flame retardant.

Embodiments of the aspect of the invention for producing the polymeric salt material will now be described, which involve the use of mixed amine neutralising agents with a phosphate ester, in conjunction with melamine to produce a polymeric salt. If the amine functionalities are pendant to an aliphatic chain then the highest neutralisation efficiency, in terms of molecular weight, can be achieved. The preferred polymeric neutralising agent is thus polyethyleneimine. This may be represented with the general structural formula:—

However, secondary and tertiary amines also are present. The monomeric unit has a molecular weight of 43 per amine functionality, which is lower than any other practical structure. The product is made by the polymerisation of ethyleneimine. The product is available in a variety of forms under the trade name Lubrisol. The most convenient industrial form is Lubrisol P which is a 50% aqueous solution of polyethyleneimine and is the commercial product of BASF.

Polytheneimine may be used as a sole precipitant for the oligomeric partial phosphate esters the results tend to be soft gels with a tendency to absorb water due to solvation. However, if mixed neutralisers are used consisting of both melamine and polyethyleneimine then a range of insoluble salts are obtained with a phosphorus content dependant on the ratio of melamine and polyethyleneimine used to totally neutralise the acid functionalities. The less melamine used to neutralise the partial phosphate esters, the higher the phosphorus content and the lower the activation temperature.

The following example illustrates a typical method for producing the Polymeric salt. In this example the partial phosphate ester is produced as given in UK application number 0310650.7 from the reaction of 2 moles of phosphorus pentoxide with 3 moles of 1-4 butane diol. This oligomer will have an acid value of 600 mg/g KOH and is known as PRP Form 1 (PRP FI).

Load a stirred vessel with cold water

Add sufficient powdered melamine to form a 5% solution

Stir and heat until the contents reach between 85° C. and 98° C. Melamine will not dissolve in hot water but if heated from cold will form a 5% solution.

Add partial phosphate ester stir and mix.

Add polyethyleneimine, stir and mix.

Maintain heat and stirring. The polymeric salt will precipitate after about 5 minutes.

Maintain heat for about 4 hours

Allow to cool and settle over night.

Decant supernatant liquor.

Refill vessel with water and stir the polymeric salt into suspension

Re heat for about 4 hours

Allow the polymeric salt to settle

Remove supernatant liquor

Refill vessel and allow polymeric salt to settle, remove supernatant liquor to leave a wet concentrate. Repeat wash once more.

The wet concentrate may be used at this stage.

In the following the product (i.e. the wet concentrate) at this stage is referred to as "polymeric sludge".

In order to produce polymeric powder, the sludge may be cake dried and then micronised by grinding, or alternatively the sludge may be spray dried. In all cases final drying must take place at 130° C. to remove the final water.

The following table shows formulations for the production of various grades of polymeric salt using the stated partial phosphate ester.

Formulations at increasing ratio of melamine to polytheneimine. Parts are by weight.

| Example | PRP F1 | Melamine | Water | Lubrisol P | Yield Solids % | P % |
|---|---|---|---|---|---|---|
| 1 | 100.0 | 27.0 | 540.0 | 73.7 | 22.1 | 12.8 |
| 2 | 100.0 | 33.8 | 675.0 | 60.1 | 18.9 | 12.8 |
| 3 | 100.0 | 40.5 | 810.0 | 64.5 | 17.0 | 12.2 |
| 4 | 100.0 | 47.3 | 945.0 | 59.3 | 15.4 | 11.9 |
| 5 | 100.0 | 54.0 | 1080.0 | 55.3 | 14.1 | 11.6 |
| 6 | 100.0 | 60.8 | 1215.0 | 50.7 | 13.0 | 11.3 |
| 7 | 100.0 | 67.5 | 1350.0 | 46.1 | 12.2 | 11.0 |

As indicated, the higher the level of melamine the greater the quantity of waste water for disposal.

PRP form 1 may alternatively be substituted with a partial phosphate ester made with the same molar ratio but substituting 1-3 propane diol, in which case the figure given in examples 1 to 7 for the PPE falls from 100 parts by weight to 95.3

Any other polymeric amine, or polyamine with a functionality of 2 or greater, may be included in the formulation with appropriate adjustment of the formulation for amine value. These additional materials alter the hardness and thereby ease the particle size reduction of the dry salts. However, no other polymeric amine can be as efficient as Lubrisol P in neutralising the orthophosphates. Further, polyamines with a lower amine content clearly add significantly more carbon to the composition of the salt, tending to both reduce the phosphorus content and raise the smoke emission on ignition. No polyamine other than melamine has found to be as efficient in lowering the solubility of the salts.

The salts may also be made by direct neutralisation of the components at elevated temperature. For this procedure a Z blade or trifoil paste mixer or any such mixer capable of dispersing thick pastes is used. The apparatus needs to able to maintain a temperature of 130° C. to 140° C. and raising the temperature of the mixture rapidly.

Example 8

The process is best illustrated by example. Using any of the formulations given in examples 1 to 7 or any other suitable combination of partial phosphate ester of carbonific polyols, melamine and polyfunctional amine, the polyfunctional amine and melamine are loaded to the mixer and the temperature raised to approximately 100° C. The mixture of amine neutralisers is thoroughly dispersed such that the melamine is dispersed evenly through out the mixture.

The partial phosphate ester (PPE) of carbonific polyols is then slowly added to the hot mixture which must be covered to prevent splashing but vented to atmosphere. Significant heat will be generated and steam will be evolved and the viscosity will increase significantly.

Once all the PPE is added, the temperature is raised to 130° C. to 140° C. and held for 15 minutes to allow the reaction to be completed.

The mixture may then either be drained from the mixer, dried and pulverised, or the mixture may be allowed to cool below 100° C. and then diluted with water to create a dispersion of the polymeric salt solids equivalent to the polymeric salt sludge produced in the above wet process. The particle size of the polymeric salt produced in this manner will be in very low and the dispersion is quite viscous.

Example 9

Thermoplastics may be rendered flame retardant by incorporating the dried polymeric salt in the master batch of the thermoplastic for extrusion or moulding. At about 30 parts by weight (pbw) incorporation the original resin such as polypropylene, polymeric salt will render the moulding or extrusion flame retardant and give a product that will pass fire performance tests for aircraft, such as FAR 25 appendix G, and will pass class B 1 according to DIN 4102. Incorporation at a lower level of about 6 pbw will easily give reaction to fire performance for less demanding fire performance measures.

Alternatively, a similar result can be obtained by coating the beads of the master batch in polymeric salt sludge. This saves the step of drying and micronising the polymeric salt. The bead is tumbled into the wet polymeric salt sludge which will cling to the surface of the thermoplastic. The bead may then be tumble dried and used in the extrusion or injection mould in the normal manner. The polymeric salt will flow into the moulding or extrusion as it is formed and become incorporated into the product with the same results as above.

The polymeric salt has been shown to be effective in most polypropylene, polyethylene and acrylics. Thus, it can be logically assumed that subject only to the limitations of processing temperatures of the thermoplastic, polymeric salt is effective in most thermosetting moulding and extrusion materials.

Example 10

Reinforced thermoplastic composites such as Twintex (made by St. Gobin, a U.S. company) or other glass or fibre reinforced composites presented as fabric, may be rendered flame retardant by drawing the woven cloth or yarn through the polymeric salt sludge. Polymeric salt does not suspend in water. Hence, the requirement is for a roller to be placed at the bottom of the sludge coating tank forcing the yarn of cloth to be drawn through the sludge. Not only does the polymeric salt cling to the polyolefin but also becomes trapped between the fibres. The cloth is then calendered to remove the excess water and polymeric salt which is allowed to flow back into the sludge tank. The cloth is then dried in an air circulating oven at between 105° C. and 150° C. The cloth may then be consolidated in the normal manner to yield a flame retardant composite, the fire performance of which is dependant on the weight of polymeric salt coated onto the unformed cloth.

If the precursor yarn is so treated it may also then be subsequently woven into cloths before subsequent consolidation into flame retardant thermoplastic composites.

Example 11

In a similar manner, woven or non woven fabrics may be flame retarded by dragging the cloth through polymeric salt sludge and subsequently drying and calendering. A polypropylene fleece treated in this manner such that the polymeric salt was applied at 40% the weight of the fleece was able to provide significant resistance to a high velocity propane burner when the treated fleece was pressed into a polypropylene surface.

Example 12

Dried polymeric salt powder was incorporated into a conventional acrylic sealant formulation where aluminium trihydrate was normally used as a flame retardant at 25% of the composition. The polymeric salt powder was able to produce the same reaction to fire performance at 8% incorporation with subsequent improvement in the acceptability of the sealant formulation. Similar behaviour is anticipated with respect to adhesive formulations where achieving flame retardancy with conventional products is not possible.

Example 13

Polymeric salt may be incorporated in latex formulations to provide intumescent coatings. The following simple formulations all produced good intumescence. However, as would be obvious to those skilled in the art, the char/foam rise height was dependant on the melt viscosity of the carrier resin. As anticipated, example 12D gave the lowest foam rise. While polymeric salt is yellow its tinting power is low and, hence, it is easily masked with ruffle titania as in example 12B. All the below examples except Example 12G are formulated at far lower pigment volume concentration (PVC) than a conventional intumescent formulation, thus giving excellent tractability and ease of manufacture, a feature not typified by conventional water based formulations.

|  | Example | | | | | | |
| --- | --- | --- | --- | --- | --- | --- | --- |
|  | 14A | 14B | 14C | 14D | 14E | 14F | 14G |
| Revacryl 344 | 89 | — | — | — | — | — | 89 |
| Pliolite LS 1 | — | 125 | — | — | — | — | — |
| Haloflex 202 | — | — | 100 | — | — | — | — |
| Silikophen P65W | — | — | — | 125 | — | — | — |
| Emultex 523 | — | — | — | — | 100 | — | — |
| Araldite PY 340-2 | — | — | — | — | — | 38.5 | — |
| Araldite HY 2992 | — | — | — | — | — | 11.5 | — |

-continued

| | Example | | | | | | |
|---|---|---|---|---|---|---|---|
| | 14A | 14B | 14C | 14D | 14E | 14F | 14G |
| Polymeric salt | 50 | 50 | 50 | 50 | 50 | 50 | 60 |
| Rutile Titania | — | 5 | — | — | — | — | 9.0 |
| Processed Mineral Fibre | — | — | — | — | — | — | 0.5 |
| 2 Butoxy Ethanol | — | — | 5 | 5 | — | — | — |

Revacryl 344 (made by Harco, a U.K. company) and Pliolite LS 1 (made by Eliochem a U.S. company) are self coalescing styrene I acrylic emulsions, Haloflex 202 (made by Zeneca, a U.K. company) is a vinyl chloride/vinylidene chloride emulsion. Silikophen P65W (made by Thomas Goldshmidt a German company) is a phenyl/methyl siloxane emulsion. Emultex 523 (made by Harco) is a VeoVa emulsion conventionally used for water based intumescent coatings. Araldite (registered trade mark) PY 340-2 is a water dispersible liquid epoxy resin and Araldite HY 2992 is the selected curing agent. 2-butoxy ethanol is used a coalescing solvent where required.

All the formulations 14A to 14F gave surface spread of flame performance that gave BS 476 part 6 index of below 12 when applied to soft wood. Formulation 14G is a formulation designed to provide protection to structural steel. When tested on a small scale test rig designed to evaluate structural steel protection formulations it gave a char form and insulation value typical of conventional formulations.

As the components of a conventional intumescent formulation are all sparingly soluble on water exposure, none of them may be exposed indefinitely without a top coat. Given that polymeric salt is insoluble it is a logical assumption that all the given formulations are stable under external exposure conditions.

Polymeric salt has also been incorporated in surface coating formulations based on polyurethanes, epoxies, and alkyds simply by stirring the powder into the commercial formulation, producing either intumescence or flame retardancy depending on the level of incorporation. Likewise, the product is easily incorporated in polyester and epoxy composites. It may also be used to enhance the fire performance of phenolic resins although little intumescence is observed.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A process for producing a flame retardant polymeric material, the process comprising:
    forming a precursor polymeric material comprising a phosphate ester in a first reaction by reacting anhydrous phosphorus pentoxide and a first reactant comprising a cyclic ether and an alcohol, the cyclic ether being selected from one or more of tetrahydrofuran and tetrahydropyran,
    subsequently forming the flame retardant polymeric material in a second reaction in which the precursor polymeric material is reacted with a second reactant that comprises a resol phenolic resin.

2. A process according to claim 1 wherein the precursor polymeric material comprises a partial phosphate ester.

3. A process according to claim 1 wherein the alcohol comprises an initiator to initiate a reaction between the anhydrous phosphorus pentoxide and the ether.

4. A process according to claim 1 wherein the alcohol comprises a chain terminator in the polymeric material.

5. A process according to claim 1 wherein the alcohol comprises a polyol having four or fewer carbon atoms.

6. A process according to claim 5 wherein the polyol comprises a diol.

7. A process according to claim 1 wherein the alcohol has a chain length of four or less carbon atoms.

8. A process according to claim 1 wherein the alcohol comprises one or more materials selected from the group consisting of methanol, ethanol, iso-propanol, N-propanol, N-butanol, iso-butanol, pentaerythritol, glycerol, trimethalolpropane, ethane diol, 1,2-propane diol, 1,3-propane diol, 1,4-butane diol, and glucose.

9. A process according to claim 1 wherein the ether is provided in a reactor vessel and the anhydrous phosphorus pentoxide and the alcohol are fed thereto.

10. A process according to claim 9 wherein the anhydrous phosphorus pentoxide is held in a holding member and is fed to the reactor by feed means comprising a conduit.

11. A process according to claim 10 wherein a screw device is mounted in the conduit to feed the anhydrous phosphorus pentoxide to the reactor vessel.

12. A process according to claim 11 wherein the feed means terminates in free space in the reactor vessel, and the method comprises feeding an inert gas to the holding member and the feed means to prevent reaction in the feed means of the anhydrous phosphorus pentoxide with the first reactant.

13. A process according to claim 9 wherein a further reactant selected from the group consisting of a cyclic ether and an alcohol is provided in the reactor vessel.

14. A process according to claim 1 wherein the first reactant comprises an alcohol, and the method comprises feeding the anhydrous phosphorus pentoxide and the alcohol to a reactor vessel until the temperature of the reaction reaches a predetermined temperature, and when such predetermined temperature is reached, halting or reducing the feeding of the anhydrous phosphorus pentoxide and the alcohol.

15. A process according to claim 14 wherein the reactor vessel includes cooling means to cool the reactants and the method comprises switching off the cooling means when the temperature of the reactants falls below the aforesaid predetermined temperature and restarting the feeding of at least one of the anhydrous phosphorus pentoxide and the alcohol.

16. A process according to claim 14 wherein the predetermined temperature lies in the range of 25° C. to 65° C.

17. A process according to claim 16 wherein the predetermined temperature lies in the range of 25° C. to 55° C.

18. A process according to claim 16 wherein the predetermined temperature lies in the range of 43° C. to 47° C.

19. A process according to claim 14 comprising heating the reaction mixture to a temperature of between 55° C. to 75° C. when all the ingredients have been added.

20. A process according to claim 1 wherein the first reactant comprises a cyclic ether and an alcohol and the anhydrous phosphorus pentoxide and the ether are in a molar ratio of anhydrous phosphorus pentoxide: ether in the range of 1:1 to 1.5:1.

21. A process according to claim 1 wherein the second reaction between the precursor polymeric material and the second reactant takes place at a temperature in the range of 30° C. to 60° C.

22. A process for producing a flame retardant polymeric material, the process comprising:

forming a precursor polymeric material comprising a phosphate ester in a first reaction by reacting anhydrous phosphorus pentoxide and a first reactant selected from the group consisting of a cyclic ether and an alcohol, the cyclic ether being selected from one or more of tetrahydrofuran and tetrahydropyran, subsequently forming the flame retardant polymeric material in a second reaction in which the precursor polymeric material is reacted with a second reactant that comprises a cyclic ether to reduce the acid value to approximately 50 mg KOH/g, and adding a cross linking agent selected from the group consisting of cycloaliphatic epoxides, poly functional aziridines, poly carbodiimides zinc ammonia complexes, and zirconium ammonia complexes.

23. A process according to claim 22 wherein the second reactant is a cyclic ether selected from the group consisting of ethylene oxide, propylene oxide and glycidol.

24. A process according to claim 22 wherein the precursor polymeric material comprises a partial phosphate ester.

25. A process according to claim 22 wherein the alcohol comprises an initiator to initiate a reaction between the anhydrous phosphorus pentoxide and the ether.

26. A process according to claim 22 wherein the alcohol comprises a chain terminator in the polymeric material.

27. A process according to claim 22 wherein the alcohol comprises a polyol having four or fewer carbon atoms.

28. A process according to claim 27 wherein the polyol comprises a diol.

29. A process according to claim 22 wherein the alcohol has a chain length of four or less carbon atoms.

30. A process according to claim 22 wherein the alcohol comprises one or more materials selected from the group consisting of methanol, ethanol, iso-propanol, N-propanol, N-butanol, iso-butanol, pentaerythritol, glycerol, trimethalolpropane, ethane diol, 1,2-propane diol, 1,3-propane diol, 1,4-butane diol, and glucose.

31. A process according to claim 22 wherein the ether is provided in a reactor vessel and the anhydrous phosphorus pentoxide and the alcohol are fed thereto.

32. A process according to claim 31 wherein the anhydrous phosphorus pentoxide is held in a holding member and is fed to the reactor by feed means comprising a conduit.

33. A process according to claim 32 wherein a screw device is mounted in the conduit to feed the anhydrous phosphorus pentoxide to the reactor vessel.

34. A process according to claim 33 wherein the feed means terminates in free space in the reactor vessel, and the method comprises feeding an inert gas to the holding member and the feed means to prevent reaction in the feed means of the anhydrous phosphorus pentoxide with the first reactant.

35. A process according to claim 31 wherein a further reactant selected from the group consisting of a cyclic ether and an alcohol is provided in the reactor vessel.

36. A process according to claim 22 wherein the first reactant comprises an alcohol, and the method comprises feeding the anhydrous phosphorus pentoxide and the alcohol to a reactor vessel until the temperature of the reaction reaches a predetermined temperature, and when such predetermined temperature is reached, halting or reducing the feeding of the anhydrous phosphorus pentoxide and the alcohol.

37. A process according to claim 36 wherein the reactor vessel includes cooling means to cool the reactants and the method comprises switching off the cooling means when the temperature of the reactants falls below the aforesaid predetermined temperature and restarting the feeding of at least one of the anhydrous phosphorus pentoxide and the alcohol.

38. A process according to claim 36 wherein the predetermined temperature lies in the range of 25° C. to 65° C.

39. A process according to claim 38 wherein the predetermined temperature lies in the range of 25° C. to 55° C.

40. A process according to claim 36 wherein the predetermined temperature lies in the range of 43° C. to 47° C.

41. A process according to claim 36 comprising heating the reaction mixture to a temperature of between 55° C. to 75° C. when all the ingredients have been added.

42. A process according to claim 22 wherein the first reactant comprises a cyclic ether and an alcohol and the anhydrous phosphorus pentoxide and the ether are in a molar ratio of anhydrous phosphorus pentoxide: ether in the range of 1:1 to 1.5:1.

43. A process according to claim 22 wherein the second reaction between the precursor polymeric material and the second reactant takes place at a temperature in the range of 30° C. to 60° C.

44. A process for producing a flame retardant polymeric material, the process comprising:

forming a precursor polymeric material comprising a phosphate ester in a first reaction by reacting anhydrous phosphorus pentoxide and a first reactant selected from the group consisting of a cyclic ether and an alcohol, the cyclic ether being selected from one or more of tetrahydrofuran and tetrahydropyran, subsequently forming the flame retardant polymeric material in a second reaction in which the precursor polymeric material is reacted with a second reactant that comprises a cyclic ether to reduce the acid value to below 7 mg KOH/g, and adding a cross linking agent selected from the group consisting of isocyanates.

45. A process according to claim 44 wherein the second reactant is a cyclic ether selected from the group consisting of ethylene oxide, propylene oxide and glycidol.

46. A process according to claim 44 wherein the precursor polymeric material comprises a partial phosphate ester.

47. A process according to claim 44 wherein the alcohol comprises an initiator to initiate a reaction between the anhydrous phosphorus pentoxide and the ether.

48. A process according to claim 44 wherein the alcohol comprises a chain terminator in the polymeric material.

49. A process according to claim 44 wherein the alcohol comprises a polyol having four or fewer carbon atoms.

50. A process according to claim 49 wherein the polyol comprises a diol.

51. A process according to claim 44 wherein the alcohol has a chain length of four or less carbon atoms.

52. A process according to claim 44 wherein the alcohol comprises one or more materials selected from the group consisting of methanol, ethanol, iso-propanol, N-propanol, N-butanol, iso-butanol, pentaerythritol, glycerol, trimethalolpropane, ethane diol, 1,2-propane diol, 1,3-propane diol, 1,4-butane diol, and glucose.

53. A process according to claim 44 wherein the ether is provided in a reactor vessel and the anhydrous phosphorus pentoxide and the alcohol are fed thereto.

54. A process according to claim 53 wherein the anhydrous phosphorus pentoxide is held in a holding member and is fed to the reactor by feed means comprising a conduit.

55. A process according to claim 53 wherein a screw device is mounted in the conduit to feed the anhydrous phosphorus pentoxide to the reactor vessel.

56. A process according to claim 55 wherein the feed means terminates in free space in the reactor vessel, and the method comprises feeding an inert gas to the holding member and the feed means to prevent reaction in the feed means of the anhydrous phosphorus pentoxide with the first reactant.

57. A process according to claim 53 wherein a further reactant selected from the group consisting of a cyclic ether and an alcohol is provided in the reactor vessel.

58. A process according to claim 44 wherein the first reactant comprises an alcohol, and the method comprises feeding the anhydrous phosphorus pentoxide and the alcohol to a reactor vessel until the temperature of the reaction reaches a predetermined temperature, and when such predetermined temperature is reached, halting or reducing the feeding of the anhydrous phosphorus pentoxide and the alcohol.

59. A process according to claim 58 wherein the reactor vessel includes cooling means to cool the reactants and the method comprises switching off the cooling means when the temperature of the reactants falls below the aforesaid predetermined temperature and restarting the feeding of at least one of the anhydrous phosphorus pentoxide and the alcohol.

60. A process according to claim 58 wherein the predetermined temperature lies in the range of 25° C. to 65° C.

61. A process according to claim 60 wherein the predetermined temperature lies in the range of 25° C. to 55° C.

62. A process according to claim 60 wherein the predetermined temperature lies in the range of 43° C. to 47° C.

63. A process according to claim 58 comprising heating the reaction mixture to a temperature of between 55° C. to 75° C. when all the ingredients have been added.

64. A process according to claim 44 wherein the first reactant comprises a cyclic ether and an alcohol and the anhydrous phosphorus pentoxide and the ether are in a molar ratio of anhydrous phosphorus pentoxide: ether in the range of 1:1 to 1.5:1.

65. A process according to claim 44 wherein the second reaction between the precursor polymeric material and the second reactant takes place at a temperature in the range of 30° C. to 60° C.

66. A process for producing a flame retardant polymeric material, the process comprising:

forming a precursor polymeric material having a structure represented by:

where R is an alkylene having 3 or 4 carbon atoms, in a first reaction by reacting anhydrous phosphorus pentoxide and a reactant comprising one or more of 1,3 propane diol and 1,4 butane diol, the anhydrous phosphorus pentoxide and said reactant being in stoichiometric ratios; and subsequently forming the flame retardant polymeric material from the precursor polymeric material in a second reaction in which the precursor polymeric material is reacted either (a) with amino resins, or (b) with a polymer having an amine functional group and melamine.

67. A process according to claim 66 wherein the diol is provided in a reactor vessel and the anhydrous phosphorus pentoxide is added to the reactor vessel by supply means.

68. A process according to claim 66 wherein the second reaction comprises reacting the precursor polymeric material with a polymer having an amine functional group and melamine, and the precursor polymeric material is a salt.

69. A process according to claim 68 wherein the process comprises reacting the precursor polymeric material and the polymer having an amine functional group with an organic amine.

70. A process according to claim 68 wherein the polymeric salt material is capable of being suspended and/or dissolved in water to provide a pH of between 4 and 8.

71. A flame retardant composition comprising a polymeric salt material formed in the process of claim 68.

72. A process according to claim 66 wherein the polymer having an amine functional group comprises polyethyleneimine.

73. A process according to claim 66, wherein the second reaction comprises reacting the precursor polymeric material with a polymer having an amine functional group and melamine, and the second reaction is carried out at a temperature of up to 100° C.

74. A process according to claim 66, wherein the second reaction comprises reacting the precursor polymeric material with a polymer having an amine functional group and melamine, and the second reaction is carried out at a temperature of between 90° C. and 150° C.

75. A process according to claim 66 wherein the phosphate ester comprises an orthophosphate.

* * * * *